US007495096B2

(12) United States Patent
Moormann et al.

(10) Patent No.: US 7,495,096 B2
(45) Date of Patent: Feb. 24, 2009

(54) PROCESSES FOR THE PRODUCTION OF CHINAZOLINE ALKALOIDS

(75) Inventors: Joachim Moormann, Werne (DE); Hans-Rainer Hoffmann, Neuwied (DE); Rudolf Matusch, Marburg (DE)

(73) Assignee: HF Arzneimittelforschung GmbH, Werne (DE)

( * ) Notice: Subject to any disclaimer, the term of this patent is extended or adjusted under 35 U.S.C. 154(b) by 225 days.

(21) Appl. No.: 10/544,265

(22) PCT Filed: Jan. 22, 2004

(86) PCT No.: PCT/EP2004/000485

§ 371 (c)(1),
(2), (4) Date: Aug. 2, 2005

(87) PCT Pub. No.: WO2004/069836

PCT Pub. Date: Aug. 19, 2004

(65) Prior Publication Data

US 2006/0084669 A1    Apr. 20, 2006

(30) Foreign Application Priority Data

Feb. 3, 2003    (DE)    ................................. 103 04 141

(51) Int. Cl.
C07D 498/00 (2006.01)
C07D 265/12 (2006.01)
C07D 265/26 (2006.01)
C07D 239/00 (2006.01)
C07D 239/70 (2006.01)
C07D 471/00 (2006.01)
C07D 487/00 (2006.01)
C07D 491/00 (2006.01)

(52) U.S. Cl. ............................. 544/91; 544/93; 544/94; 544/249; 544/250

(58) Field of Classification Search ................. 544/249, 544/250, 91, 93, 94
See application file for complete search history.

(56) References Cited

U.S. PATENT DOCUMENTS 6,436,937 B1    8/2002    Asmussen et al.
6,548,510 B1    4/2003    Asmussen et al.
6,599,511 B1    7/2003    Asmussen et al.

FOREIGN PATENT DOCUMENTS

| DE | 199 06 975 | 4/2004 |
| DE | A 199 06 975 | 4/2004 |
| DE | 199 06 978 | 7/2004 |
| DE | 199 06 979 | 7/2004 |
| DE | A 199 06 978 | 7/2004 |
| DE | A 199 06 979 | 7/2004 |

OTHER PUBLICATIONS

Yadav, et al., Microwave-assisted Rapid Synthesis of the Cytotoxic Alkaloid Luotonin A, Tetrahedron Letters, vol. 43, 1905-07 (2002).*
Späth, et al., On Derivatives of Peganin and their Ring Homologs. VIII. Communications on Peganin, Ber. 68, 2221-24 (1935).*
Yadav, et al., Microwave-assisted rapid synthesis of the cytotoxic alkaloid luotonin A, Tetrahedron Letters, 43, 1905-07 (2002).*
Späth & Platzer (Ber. 68 (1935), 2221-2224.
Morris, et al., *J. Amer. Chem. Soc.*; 57 (1935) p. 951-954.
Sargazakav, et al.; *Khim. Prir. Soedin.*; 4 (1990), p. 506-507.
Jen, T., et al.; "Amidines. 5. Synthesis of Pyrrolo '2, 3-b isoquinoline, Imidazo '1, 2-b isoquinoline, Pyrrolo '2, 1-b quinazoline, and 1,3 Thiazino '2,3-b quinazoline Derivatives and Related Heterocycles as Potential Antihypersensitive Agents;" *Journal of Medicinal Chemistry*; vol. 16, No. 6 (1973), p. 633-637.
Yadav, J.S. & Reddy, B.V.S.; "Microwave-Assisted Rapid Synthesis of the Cytotoxic Alkaloid Luotonin A;" *Tetrahedron Letters*; vol. 43 (2002) p. 1905-1907.
Späth and Platzer, *On Derivatives of Peganin and Their Ring Homologs*, (VIII. Communications on Peganin), 2nd Chemical Laboratory, University of Vienna, received Oct. 19, 1935 (with English translation).
Morris, R.C. et al., *Structure of Vasicine. III. Position of the Hydroxyl Group*[1], Position of the Hydroxyl Group in Vasicine, The Chemical Laboratory of the University of Illinois, May, 1935.
Sargazakov, K.D. et al.. *Preparation of Deoxypeganine Hydrochloride*, Institute of Chemistry of Plant Substances, Academy of Sciences of the Uzbek SSR, Tashkent, Translated from Khimiya Prirodnykh Soedinenii, No. 4, pp. 506-507, Jul.-Aug. 1990. Original article submitted Nov. 13, 1989.

* cited by examiner

*Primary Examiner*—James O Wilson
*Assistant Examiner*—Erich A Leeser
(74) *Attorney, Agent, or Firm*—D. Peter Hochberg; Sean F. Mellino; Daniel J. Smola

(57) ABSTRACT

Processes for the production of a compound of the following formula (I)

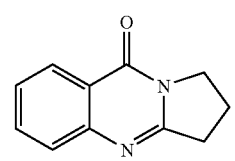

(I)

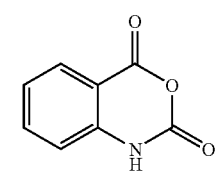

(II)

by converting a compound of formula (II) with 2-pyrrolidone used in excess relative to compound (II) and processes for the production of a compound of formula (III).

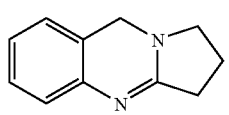

(III)

The latter process includes preparing compound (I); a reduction reaction which yields compound (III) in salt form; and liberating compound (III) from the salt.

22 Claims, No Drawings

PROCESSES FOR THE PRODUCTION OF CHINAZOLINE ALKALOIDS

BACKGROUND OF THE INVENTION

CROSS-REFERENCE TO RELATED APPLICATIONS

This application is a National Stage application of International Application No. PCT/EP2004/000485, filed on Jan. 22, 2004, which claims priority of German application number 103 04 141.9, filed on Feb. 3, 2003.

1. Field of the Invention

The present invention refers to processes for the production of chinazoline alkaloids of the following formulas (I) and (III).

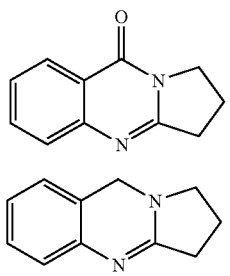

2. Description of the Prior Art

Compound (III) is 1,2,3,9-tetrahydropyrrolo[2,1-b]chinazoline. This compound is also known under the trivial name of deoxypeganine and occurs in plants of the Zygophyllaceae family. Because of its pharmacological properties, deoxypeganine is regarded as a member of the group of reversibly active cholinesterase inhibitors.

Apart from this, it also acts as a monoamine oxidase inhibitor. Deoxypeganine is taken into consideration as a medicinal agent for therapeutic purposes, e.g. for treating drug addiction and drug dependence (DE-A 199 06 978), for the therapy of Alzheimer's dementia (DE-A 199 06 975), or for the therapy of nicotine dependence (DE-A 199 06 979).

Compound (I), known under the designation of pegen-(9)-one-(8), is an important intermediate product in the synthesis of deoxypeganine and other chinazoline alkaloids of this type. The synthesis of pegen-(9)-one-(8) (short: pegenone) can be performed according to SPÄTH and PLATZER (Ber. 68 (1935), 2221-2224) by converting isatoic acid anhydride with an equimolar amount of pyrrolidone. Subsequently, a high-vacuum distillation at 140 to 160° C. must be carried through in order to separate the reaction byproducts. This method is suitable only for small amounts (in the gram range), but not for production on a larger scale.

According to MORRIS, HANFORD and ADAMS (J. Amer. Chem. Soc. 57 (1935), 951-954), pegenone (2,3-trimethylene-4-chinazolone) can be obtained (i) by oxidation of deoxyvasicine by means of hydrogen peroxide. Deoxyvasicine is identical with deoxypeganine. Alternatively, (ii), pegenone can be obtained by multistage synthesis, with γ-phenoxybutyryl chloride being reacted with o-aminobenzamide to the corresponding amide. After ring closure under heating, the phenoxyl group is replaced by bromine, and subsequently, through a further ring closure, 2,3-trimethylene-4-chinazolone (=pegenone) is obtained.

If pegenone is required as a starting compound for the production of deoxypeganine, the only method that could be taken into consideration—apart from the method according to SPÄTH and PLATZER mentioned above—is, if at all, the synthesis method (ii) proposed by Morris et al. This method, however, is uneconomical due to the number of reaction steps.

Deoxypeganine is preferably obtained by isolation from Syrian rue (*Peganum harmala*), or by synthesis.

MORRIS, HANFORD and ADAMS (loc cit., p. 953) describe the production of deoxyvasicine (=deoxypeganine) by reduction of 2,3-α-hydroxytrimethylene)-4-chinazolone or 2,3-(α-chlorotrimethylene)-4-chinazolone, using glacial acetic acid and zinc dust (reaction type: Clemmensen reduction). Following chloroform extraction, the product was isolated by crystallisation from petroleum ether. It is disadvantageous here that the starting compounds (2,3-(α-hydroxytrimethylene)-4-chinazolone or 2,3-(α-chlorotrimethylene)-4-chinazolone) have to be synthesized starting from peganine (=vasicine).

According to SARGAZAKOV et al. (Khim. Prir. Soedin. 4 (1990), 506-507), deoxypeganine hydrochloride can be obtained by cyclocondensation of anthranilic acid with 2-pyrrolidone to give deoxyvasicinone hydrochloride (=pegenone hydrochloride) and subsequent Clemmensen reduction of this intermediate product to give deoxypeganine hydrochloride. The cyclocondensation reaction is performed in the presence of phosphorus trichloride, with toluene being used as solvent. Both after the first step (cyclocondensation) and after the second step (reduction), multiple chloroform extractions are necessary. Altogether, the production of 2 kg of deoxypeganine hydrochloride requires approx. 50 l of toluene and 80 l of chloroform.

The synthesis method described by SARGAZAKOV et al. is disadvantageous for several reasons. The yield amounts to only approx. 50%, the product obtained (deoxypeganine hydrochloride) being of a purity of 94-95%. This method requires large amounts of organic solvents, especially toluene and chloroform, as well as phosphorus trichloride. This is disadvantageous for reasons of ecology, but also for reasons of safety and cost. In addition, this method requires great expenditure of time and work since several chloroform extraction steps have to be carried through in order to achieve the aforementioned degree of purity. With a view to the use of deoxypeganine as medicinal agent it is especially disadvantageous that chlorohydrocarbons are used.

In the above-mentioned known synthesis methods, it is furthermore disadvantageous that due to the high proportion of reaction byproducts, isolation of the products by crystallisation methods is not possible and can instead be attained only by costly extraction steps or high-vacuum distillation.

SUMMARY OF THE INVENTION

It was therefore an object of the present invention to indicate synthesizing processes for the production of chinazoline alkaloids of the above-indicated formulas (I) and (III) which
- enable yields and degrees of product purity which at least correspond to those of known processes, or which surpass them;
- enable the production of deoxypeganine (III) for use in the manufacture of medicaments;
- largely do without the use of substances which are damaging to the environment or to health, especially organic solvents;
- have a good raw material balance;

substantially produce only such byproducts as can be readily recycled;

can be carried through using cost-effective starting materials; and altogether enable a simpler and more cost-effective production of the above mentioned compounds on an industrial scale.

These and other objects are surprisingly achieved by methods according to the independent claims 1, 9, 18 and 20, as well as by the further embodiments described in the dependent claims.

DETAILED DESCRIPTION OF THE PRESENT INVENTION

According to claim 1, in a process according to the invention, a compound of formula (II) (=isatoic acid anhydride)

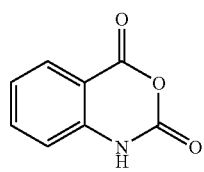

is reacted with 2-pyrrolidone (=pyrrolidinone) to obtain a compound of formula (I). In this reaction, an excess of 2-pyrrolidone is used, relative to the amount of compound (II) used. This means that the amount of pyrrolidone used is larger than the equimolar amount. For example, 1.5 to 5 mol, especially 2 to 4 mol, or even 2.5 to 3.5 mol, of pyrrolidone are used, each of these values relating to the amount of compound (II) used.

This surprisingly has as a consequence that the formation of unfavourable reaction products is reduced and that the nascent product (I) can be readily crystallized. In addition, it is possible to obtain high yields (70%), with purity at approximately 99% (NMR). Due to the excellent crystallizability, it is possible to dispense with expensive purification methods, such as high-vacuum distillation.

Since purification of the product can be achieved in a simple manner by crystallization, the process can also be carried through on a larger scale without any problems.

The process is based on the following reaction equation, presented by way of example:

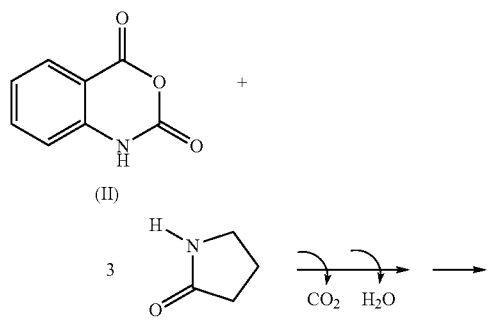

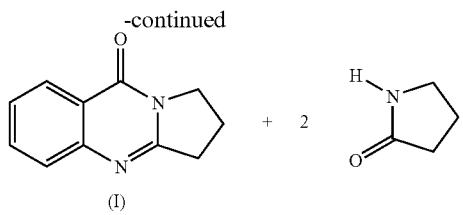

The reaction is performed under addition of heat, such as at temperatures in the range of 50 to 200° C. The initial temperature may be in the range of 70 to 130° C., and subsequently a temperature in the range of 140 to 200° C. is maintained; for example, the temperature is initially 80 to 120° C., and later is 150 to 190° C.

The aforementioned initial temperature may be maintained for a period of 0.5 to 2 hours, especially 1 to 1.5 hours, after the start of the reaction. The aforementioned subsequent temperature is maintained for a period of 1 to 8 hours, especially 2 to 5 hours.

The process is carried through by providing pyrrolidone and thereafter adding thereto the compound (II) in portions.

It is particularly advantageous to isolate product (I) directly from the reaction mixture by crystallisation. To crystallize compound (I), the reaction mixture is left to cool and is seeded with seed crystals. Crystallization is carried through at room temperature, such as at least 25° C., with preference 30 to 70° C., or even 40 to 60° C., whereby the course of the crystallization is accelerated. The crystallization process takes approximately 24 hours to 7 days, preferably approximately 50 hours to 100 hours. The resultant crystals contain pyrrolidone.

The present invention further relates to processes for the production of deoxypeganine (compound according to formula III). The processes substantially comprise three steps:

Producing compound (1) according to a process according to the present invention;

a reduction reaction, giving compound (III) in salt form; and liberating compound (III) from the salt.

The course of the reduction reaction (Clemmensen reaction) can be indicated, by way of example, as follows:

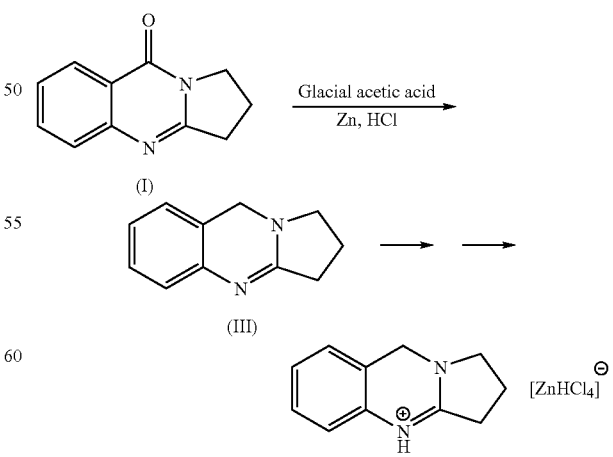

Compound (III) is here obtained in the form of a salt; in the case presented above by way of example, tetrachlorozincate salt is obtained if the reduction reaction is carried through in the presence of glacial acetic acid, zinc, and hydrochloric acid.

Particularly, the starting compound (I) used is a reaction product isolated by crystallisation and this reaction product can be obtained by the above-described processes.

According to one embodiment of the invention, the reduction reaction is performed using glacial acetic acid, zinc (zinc dust) and hydrochloric acid, which is done by initially dissolving compound (I) in glacial acetic acid and subsequently adding zinc and hydrochloric acid.

According to an alternative embodiment of the present invention, the reduction reaction is performed under addition of zinc (as zinc dust) and sulfuric acid, without use of glacial acetic acid. This yields the hydrogen sulfate of compound (III):

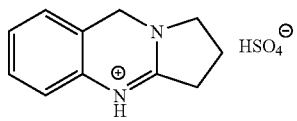

The reaction is carried through at temperatures of approximately 50 to 90° C., especially 70 to 80° C.; generally, the reaction has quantitatively terminated after about 2 to 3 hours. After termination of the reaction, the excess zinc is removed by known methods, e.g. by colation.

The salt of compound (III) thus obtained can be isolated in a simple and efficient manner by crystallisation from the reaction mixture. For this purpose, the reaction mixture is seeded with seed crystals. When the crystallisation has taken place, the remaining mother liquor is separated by methods known to those skilled in the art (e.g. decanting).

In the above-mentioned step (C) of the inventive processes for the production of a compound of formula (III), the salt obtained in step (B) is then converted to the free base (III).

This is generally done by adding a base, preferably NaOH, to an aqueous solution of the salt.

According to one embodiment of the present invention, this step is carried out in such a manner that the liberated base is obtained in molten form. This is achieved by carrying through the reaction at a temperature that is higher than the melting point (86° C.) of the free base (III) (=deoxypeganine) at temperatures in the range of from 90 to 100° C. The base present in molten form can be separated in a simple manner, possibly after freezing, from the reaction mixture. Methods suitable for this purpose are known to those skilled in the art.

According to a further embodiment, the molten base (III) is thereafter cooled down and left to freeze. The frozen product is dissolved to obtain a saturated solution and water is used as the solvent. From this saturated solution, which is adjusted so as to be alkaline by addition of a base (such as NaOH), the final product deoxypeganine can be isolated in high-purity form through the subsequent crystallisation process.

The invention thus extends to processes for the production of deoxypeganine (compound of formula (III)) which contain a step wherein the compound is separated from the reaction mixture in liquid form. More particularly, the invention encompasses production processes of the kind mentioned which contain the following process steps:

reducing the mentioned compound (I) to compound (III), whereby compound (III) is formed in salt form;

adding of a base, whereby compound (III) is liberated from the salt and separates out in liquid form.

The inventive processes enable a simple and economical manufacture of the mentioned compounds (I, III) in a quantity and purity required in the production of medicaments. It is particularly advantageous here that the use of organic solvents can be dispensed with.

The processes according to the invention will in the following be illustrated by examples.

EXAMPLE 1 (COMPARISON EXAMPLE)

Preparation of pegen-9-(one)-(8) (identical with formula (I)) by converting pyrrolidone with an equimolar amount of isatoic acid anhydride according to SPÄTH and PLATZER (loc cit., p. 2221) and 2224.

Two liters liters of pyrrolidone were heated with 4 kg of isatoic acid anhydride (molar quantity ratio 1:1.07), in a chrome steel vessel (receptivity: 10 l), under vigorous stirring, to 120° C. until incipient gas formation. This was followed by heating for 10 minutes to 160° C. and subsequently for 30 minutes to 190° C. Of this reaction mixture, 558 g (=3 mol) was transferred, in still hot-liquid state, into a 1-liter flask (NS 29). The residue remaining in the steel vessel froze to a black, glassy mass which is not suitable for isolation of pegenone.

From the reaction mixture (558 g) transferred into the flask, up to 117 g of pegenone could be distilled by high-vacuum distillation using a distillation condenser that was heated to 120° C. This corresponds to a yield of 21%. After recrystallization from ether, a melting point of 111° C. was determined.

EXAMPLE 2

Synthesis of Pegenone (Compound According to Formula (I)

One mole of isatoic acid anhydride (formula (II)) was converted with 3 mol of pyrrolidone. To this end, pyrrolidone was placed in a heatable chrome steel drum (30 liters) and heated to approximately 100° C., subsequently isatoic acid anhydride was added in portions while stirring continuously.

After approximately 1 hour, the entire amount of isatoic acid anhydride was dissolved in pyrrolidone. This was followed by heating for 5 hours up to 155 to 160° C. (during this process, $CO_2$ and $H_2O$ was formed; see above) and finally by heating for a short time up to 170 to 180° C.

After cooling to approximately 50° C., the mass thus obtained was seeded with pegenone crystals and left to crystallise for approximately 50 to 100 hours at room temperature. By increasing the temperature (at least 25° C.), the crystallisation process could be accelerated (duration only approximately 2 to 3 days). The "mother liquor" was separated from the crystals by decanting.

Altogether, more than 90% of the starting compounds used were converted to pegenone. The yield of crystallised pegenone was 40%; the remaining portion of the pegenone is dissolved in pyrrolidone. The pegenone crystals obtained still have a content of 30%-mol of pyrrolidone, according to NMR; the purity of the pegenone is approximately 99% according to NMR.

In a modification of this process, the starting compounds were used in a quantity ratio of 1:2.5 (isatoic acid anhydride: pyrrolidone). The proportion of the crystallised pegenone could thereby be increased to approximately 55%, at a purity of approximately 99%.

EXAMPLE 3

Clemmensen Reduction of Compound (I)

The pegenone crystals prepared according to Example 2 (2.5 kg) with a content of 15%-wt of pyrrolidone. This corresponds to 1.83 kg or 9.81 mol of pure pegenone) were dissolved at approximately 50° C. in 6.1 l (=100.4 mol) of glacial acetic acid and transferred into a chrome steel vessel (50 liters). Subsequently, 3.7 kg (=56.4 mol) of zinc dust was added in small portions, during which process the temperature of the reaction mixture was kept at approximately 60° C. After approximately 1 hour, 4×3 liter of concentrated HCl (32%; corresponding to 121.74 mol) were added, in small portions, within 2 hours while stirring continuously. Thereafter (after approximately 4 to 5 hours) the excess zinc dust was removed from the reaction mixture by colation. After seeding with seed crystals, approximately 66% of the deoxypeganine salt could be separated by crystallization. The remaining mother liquor was narrowed down by evaporation, whereupon 66% of the deoxypeganine salt again crystallized. Altogether, approximately 90% of the deoxypeganine salt could be obtained in crystalline form.

b) Liberation of Deoxypeganine Base (Compound (III))

Crystals (2.5 kg) obtained in this manner were dissolved in hot water (approximately 11 liters). Subsequently, NaOH was added under stirring (approximately 8 kg rotulae), while heating the mixture to 95 to 100° C. This yielded deoxypeganine in molten form, and this was separated from the reaction mixture. After freezing, the product was again dissolved in heated water to obtain a saturated solution, which solution was adjusted with NaOH so as to be alkaline. From this saturated alkaline solution, deoxypeganine was isolated by crystallisation.

The deoxypeganine yield, relative to the deoxypeganine salt, was more than 90%, with a purity of 99.9% (NMR).

EXAMPLE 4

Clemmensen Reduction of Compound (I)
(Alternative Method)

175 g pegenone crystals (containing 30%-mol of pyrrolidone; this corresponds to 150 g of pegenone; see Example 2) were mixed with 750 ml of (20%) $H_2SO_4$ and heated (approximately 85° C.) for approximately 30 min while stirring.

Subsequently, 260 g of zinc dust was gradually added (duration: approximately 2 hours). After approximately 1 hour, $H_2SO_4$ was added again (375 ml, 40%). After a total of approximately 3 hours, the reaction had terminated, and the excess zinc was separated by colation.

As described under Example 3 a), the deoxypeganine salt obtained was separated from the reaction mixture by crystallisation. The liberation of the base was carried through according to the method described under Example 3 b).

What has been described above are preferred aspects of the present invention. It is of course not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, combinations, modifications, and variations that fall within the spirit and scope of the appended claims.

The invention claimed is:

1. A process for producing a compound or reaction product of the following formula (I)

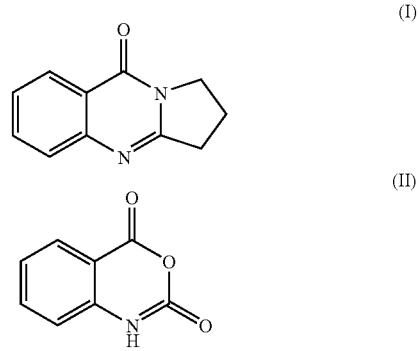

comprising the steps of:
converting a compound of formula (II) with 2-pyrrolidone in an amount of 1.5 to 5 mol relative to the amount of compound (II) to form a reaction mixture;
heating said reaction mixture to an initial temperature of 70° C. to 130° C.;
maintaining said initial temperature for a period of 0.5 to 2 hours;
subsequently heating said reaction mixture to a subsequent temperature of 140° C. to 200° C.;
maintaining said subsequent temperature for a period of 1 to 8 hours; and
crystallizing said reaction product (I) to isolate said reaction product (I) directly from said reaction mixture.

2. The process according to claim 1, wherein said process comprises using 2-pyrrolidone in an amount of 2 to 4 mol relative to the amount of compound (II).

3. The process according to claim 2, wherein said process comprises using 2-pyrrolidone in an amount of 2.5 to 3.5 mol relative to the amount of compound (II).

4. The process according to claim 1, wherein said process comprises the step of initially heating said reaction mixture to an initial temperature of 80 to 120° C. and subsequently heating said reaction mixture to a subsequent temperature of 150 to 190° C.

5. The process according to claim 1, wherein said process comprises the step of maintaining said initial temperature for a period of 1 to 1.5 hours and maintaining said subsequent temperature for a period of 2 to 5 hours.

6. The process according to claim 1, further comprising the steps of:
cooling said reaction mixture;
seeding said reaction mixture, after cooling, with seed crystals of compound (I); and
maintaining said reaction mixture seeded with said seed crystals at room temperature for a period of 24 hours to 7 days to enable crystallisation.

7. The process according to claim 6, comprising the step of maintaining said reaction mixture seeded with said seed crystals at a temperature of at least 25° C. for a period of 50 to 100 hours to enable crystallisation.

8. The process according to claim 7, wherein said crystallisation is carried through at a temperature of 30 to 70° C.

9. The process according to claim 8, wherein said crystallisation is carried through at a temperature of 40 to 60° C.

10. A process for producing a compound of formula (III),

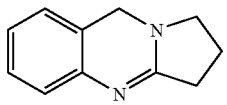
(III)

said process comprising the steps of:
(A) preparing a compound of formula (I) by converting a compound of formula (II)

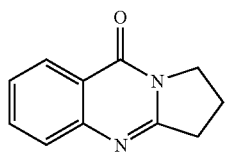
(I)

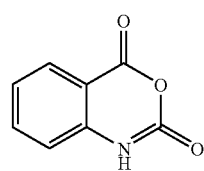
(II)

with 2-pyrrolidone in an amount of 1.5 to 5 mol relative to the amount of compound (II);
(B) crystallizing compound (I) to isolate compound (I) directly from the reaction mixture;
(C) performing a reduction reaction to provide said compound (III) in salt form; and
(D) liberating compound (III) from the salt.

11. The process according to claim 10, comprising the step of performing said reduction reaction (step C) in the presence of zinc and acid.

12. The process according to claim 11, comprising the step of initially dissolving said compound (I) in glacial acetic acid and subsequently adding zinc and hydrochloric acid to said compound (I) dissolved in glacial acetic acid.

13. The process according to claim 12, comprising the step of performing said reduction reaction in the presence of aqueous sulfuric acid and zinc dust.

14. The process according to claim 10, further comprising the step of, subsequent to step (C), isolating said compound (III) as a salt by crystallisation from said reaction mixture.

15. The process according to claim 10, further comprising the step of, in step (D), adding a base to said reaction mixture to liberate said compound (III) from the salt.

16. The process according to claim 15, wherein said base is NaCH.

17. The process according to claim 15, wherein step (D) is carried through under heating, and further comprising the step of obtaining said compound (III), which is liberated from the salt in molten form.

18. The process according to claim 17, further comprising the step of cooling down said compound (III) present in molten form by freezing and, after freezing, crystallizing said compound (III) from an aqueous alkaline solution.

19. The process according to claim 10, wherein said compound (III) is liberated from the salt in molten form.

20. The process according to claim 19, further comprising the step of cooling down said compound (III) present in molten form to freezing and subsequently crystallizing said compound (III) from an aqueous alkaline solution.

21. The process according to claim 19, further comprising the step of separating said compound (III) from the reaction mixture in liquid form.

22. The process according to claim 21, further comprising the following steps:
reducing said compound (I) to compound (III) to provide said compound (III) in salt form; and
adding a base to said compound (III) to liberate said compound (III) from the salt and to separate said compound (III) out in liquid form.

* * * * *